United States Patent
Du et al.

(10) Patent No.: US 8,486,268 B2
(45) Date of Patent: Jul. 16, 2013

(54) PRECISION PEAK MATCHING IN LIQUID CHROMATOGRAPHY-MASS SPECTROSCOPY

(75) Inventors: Peicheng Du, Montvale, NJ (US); Frank Suits, Garrison, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 13/406,956

(22) Filed: Feb. 28, 2012

(65) Prior Publication Data
US 2012/0158316 A1 Jun. 21, 2012

Related U.S. Application Data

(62) Division of application No. 12/547,874, filed on Aug. 26, 2009, now Pat. No. 8,158,003.

(51) Int. Cl.
*B01D 15/08* (2006.01)
(52) U.S. Cl.
USPC ........ 210/656; 210/143; 210/198.2; 436/161; 702/32
(58) Field of Classification Search
USPC .. 210/656, 101, 143, 198.2; 436/161; 702/19, 702/22, 30, 32
See application file for complete search history.

(56) References Cited

U.S. PATENT DOCUMENTS

| 7,056,434 | B2 | 6/2006 | van der Greef et al. |
| 7,635,433 | B2 | 12/2009 | Li |
| 2002/0009756 | A1 | 1/2002 | Mandell et al. |
| 2002/0053545 | A1 | 5/2002 | van der Greef |
| 2003/0139885 | A1 | 7/2003 | Brock et al. |
| 2007/0055458 | A1 | 3/2007 | Jarman et al. |
| 2011/0049349 | A1 | 3/2011 | Du et al. |

FOREIGN PATENT DOCUMENTS

WO 2007112289 10/2007

OTHER PUBLICATIONS

America et al., "Comparative LC-MS: A landscape of peaks and valleys", Proteomics (Feb. 2008) pp. 731-749, vol. 8.
Anderle et al., "Quantifying reproducibility for differential proteomics: noise analysis for protein liquid chromatography-mass spectrometry of human serum", Bioinformatics (Jul. 2004) pp. 3575-3582, vol. 20.
Bellew et al., "A suite of algorithms for the comprehensive analysis of complex protein mixtures using high-resolution LC-MS", Bioinformatics (Aug. 2006) pp. 1902-1909, No. 15.

(Continued)

*Primary Examiner* — Ernest G Therkorn
(74) *Attorney, Agent, or Firm* — Scully, Scott, Murphy & Presser, P.C.; Vazken Alexanian

(57) ABSTRACT

A method that identifies common peaks among unidentified peaks in the data from different LC-MS or LC-MS/MS runs is provided. The method employs an algorithm, herein referred to as "Precision Peak Matching (PPM)." The different runs can be from different laboratories, instruments, and biological samples that result in a significant variability in the data. PPM allows estimation and control of precision, defined as the fraction of truly identical peptide pairs among all pairs retrieved, in the matching process. PPM finds the maximal number of peptide pairs at a prescribed precision, thereby allowing quantitative control over the trade off between the number of true pairs missed, and false pairs found. PPM finds common peptides from a database of LC-MS runs of heterogeneous origins, and at the specified precision. PPM fills a much-needed role in proteomics by extracting useful information from disparate LC-MS databases in a statistically rigorous and interpretable manner.

20 Claims, 9 Drawing Sheets

OTHER PUBLICATIONS deGroot et al., "Post alignment clustering procedure for comparative quantitative proteomics LC-MS Data", Proteomics (Jan. 2008) pp. 32-36, vol. 8.

Jaffe et al., "PEPPeR, a Platform for Experimental Proteomic Pattern Recognition", Molecular & Cellular Proteomics (Oct. 2006) pp. 1927-1941, vol. 5.

Koyutürk et al., "Pairwise Local Alignment of Protein Interaction Networks Guided by Models of Evolution", RECOMB (2005) pp. 48-65.

Li et al., "A Software Suite for the Generation and Comparison of Peptide Arrays from Sets of Data Collected by Liquid Chromatography-Mass Spectometry", Molecular & Cellular Proteomics (Sep. 2005) pp. 1328-1340, vol. 4, No. 9.

Masselon et al., "Influence of mass resolution on species matching in accurate mass and retention time (AMT) tag proteomics experiments", Rapid Commun. Mass Spectrom. (Apr. 2008) pp. 986-992, vol. 22, No. 7.

May et al., "A Platform for Accurate Mass and Time Analyses of Mass Spectrometry Data", Journal of Proteome (Jun. 2007) pp. 2685-2694, vol. 6, No. 7.

Noy et al., "Robust Estimation and Graph-based Meta Clustering for LC-MS Feature Extraction" IEEE International Conference on Bioinformatics and Biomedicine (Nov. 2007) pp. 230-236.

Smith et al., "An accurate mass tag strategy for quantitative and high-throughput proteome measurements" Proteomics (May 2002) pp. 513-523, vol. 2, No. 5.

Sudha et al., "Global proteomic analysis distinguishes biologic differences in head and neck squamous carcinoma", Laboratory Investigation (Nov. 2007) pp. 755-766, vol. 87.

Wang et al., "Quantification of Proteins and Metabolites by Mass Spectrometry without Isotopic Labeling or Spiked Standards", Analytical Chemistry (Sep. 15, 2003) pp. 4818-4826, vol. 75, No. 18.

Yu et al., "Multiple Peak Alignment in Sequential Data Analysis: A Scale-Space-Based Approach", IEEE/ACM Transactions on Computational Biology and Bioinformatics (Jul.-Sep. 2006) vol. 3, No. 3.

PRECISION PEAK MATCHING IN LIQUID CHROMATOGRAPHY-MASS SPECTROSCOPY

CROSS REFERENCE TO RELATED APPLICATION

This application is a divisional of U.S. patent application Ser. No. 12/547,874, filed Aug. 26, 2009, now U.S. Pat. No. 8,158,003 the entire content and disclosure of which is incorporated herein by reference.

BACKGROUND

The present invention generally relates to methods of matching peaks in datasets from a plurality of liquid chromatography-mass spectroscopy and apparatuses for the same.

Liquid chromatography-mass spectroscopy (LC-MS) is an analytical chemistry technique that combines the physical separation capabilities of liquid chromatography with the mass analysis capabilities of mass spectrometry. Optionally, LC-MS may employ tandem mass spectroscopy (MS/MS), in which multiple mass spectrometry steps are employed with at least one intervening fragmentation step between the multiple mass spectroscopy steps. Liquid chromatography in combination with tandem mass spectroscopy is typically referred to as liquid chromatography-tandem mass spectroscopy (LC-MS/MS), and is a subset of LC-MS.

Data from a liquid chromatography-mass spectroscopy is typically generated as "features" in a multi-dimensional space including a mass-to-charge ratio of a detected material as one axis and a retention time of the detected material as another axis. The retention time is the time it takes for a material to travel through a capillary column that leads into a vacuum environment in which the material is ionized for detection by a mass spectrometer. The mass-to-charge ratio is the ratio of the mass of the material to the electrical charge of the material as detected by a mass spectrometer after the material is ionized in a vacuum environment. In its simplest form, a feature is simply a peak in the LC-MS chromatogram, but a feature may also be a monoisotopic mass deduced from an isotope series, with corresponding retention time and optional intensity.

Multiple LC-MS runs result in multiple datasets, in which each dataset includes a list of peaks from one LC-MS run. The list of peaks is represented in the multi-dimensional space of a mass-to-charge ratio, a retention time, and optionally, an intensity of the peak. It is a challenge to compare proteomics data from different LC-MS experiments because not all the peaks coincide with corresponding peaks from other runs in the multi-dimensional space of the mass-to-charge ratio and the retention time.

There is an increasing need for computational methods to compare protein expression measured by LC-MS or LC-MS/MS proteomics experiments. Public domain proteomic databases such as the Open Proteomic Database and PeptideAtlas have accumulated thousands of LC runs from various laboratories, and the numbers continue to increase. Comparisons of multiple proteomic experiments based on identified proteins and peptides are feasible, but limited because most LC-MS or LC-MS/MS peaks are unidentified and therefore overlooked. In addition, many peaks in LC-MS/MS are unidentified because peptide identification by MS/MS ion search is still a low percentage sampling process with imperfect reproducibility.

Without sequence information, the common practice is to match peptides between different runs based solely on similarity in mass and normalized retention time. However, this method is prone to some level of mismatches because different peptides may share similar mass and normalized retention times by chance. Thus, peptide matching based on mass and retention time similarity should be accompanied by error rate estimation, especially for complex protein mixture.

The error rate in matching is largely overlooked in the literature. Some of the few references that consider the error rate in matching include Jaffe, J. D. et al., "PEPPeR, a platform for experimental proteomic pattern recognition," Mol. Cell. Proteomics 5, 1927-1941 (2006), Monroe, M. E. et al., "VIPER: an advanced software package to support high-throughput LC-MS peptide identification," Bioinformatics 23, 2021-2023 (2007), and Anderson, K. K., Monroe, M. E. & Daly, D. S., "Estimating probabilities of peptide database identifications to LC-FTICR-MS observations," Proteome Sci 4, 1 (2006). The PEPPeR pipeline estimates the mismatching rate by bootstrapping, while VIPER estimates the probability of correct matching by Expectation Maximization (EM). VIPER uses Accurate Mass and Time Tag (AMT) peptide identification, which matches mass and retention time pairs to a database of identified peptides. VIPER estimates the mismatching rate by searching against the database of identified peptides where every mass is shifted by a constant amount, such as 7 Dalton (Da.). However, for both PEPPeR and VIPER, the accuracy of the estimated mismatching rates is unclear, and require some peptides to be identified. More importantly, both are limited to comparison among similar proteomic experiments.

BRIEF SUMMARY

In an embodiment of the present invention, a method that identifies common peaks among unidentified peaks in the datasets from different LC-MS or LC-MS/MS runs is provided. The method employs an algorithm that is herein referred to as "Precision Peak Matching," or "PPM." The different runs can be from different laboratories, instruments, and biological samples that result in a significant variability in the data. PPM can be employed during matching of two peak lists from two different LC-MS runs.

According to an aspect of the present invention, a system for matching peaks in liquid chromatography-mass spectroscopy (LC-MS) datasets from multiple runs is provided. The system includes a memory and a processor device in communication with the memory. The system is configured to perform a method including generating, by employing the processor and the memory, an aligned query list for peaks from a first dataset from a first LC-MS run; generating, by employing the processor and the memory, a target peak list for peaks from a second dataset from a second LC-MS run; generating, by employing the processor and the memory, a mass-to-charge ratio (m/z) tolerance parameter and a retention time (Rt) tolerance parameter that satisfy a specification input criterion for a false matching rate between the aligned query list and the target peak list; determining, by employing the processor and the memory, a true matching rate between the aligned query list and the target peak list employing the m/z tolerance parameter and the Rt tolerance parameter; selecting, by employing the processor and the memory, an optimized m/z tolerance value and an optimized Rt tolerance value by repeating the step of selecting the m/z tolerance parameter and Rt tolerance parameter and the step of determining the true matching rate; and generating, by employing the processor and the memory, an optimal list of matches among peaks across the aligned query list and the target peak list employing the optimized m/z tolerance value and the optimized Rt tolerance value as matching parameters.

According to another aspect of the present invention, a method for matching peaks in liquid chromatography-mass spectroscopy (LC-MS) datasets from multiple runs is provided. The method includes generating, by employing the processor and the memory, an aligned query list for peaks from a first dataset from a first LC-MS run, generating, by employing the processor and the memory, a target peak list for peaks from a second dataset from a second LC-MS run; generating, by employing the processor and the memory, a mass-to-charge ratio (m/z) tolerance parameter and a retention time (Rt) tolerance parameter that satisfy a specification input criterion for a false matching rate between the aligned query list and the target peak list; determining, by employing the processor and the memory, a true matching rate between the aligned query list and the target peak list employing the m/z tolerance parameter and the Rt tolerance parameter; selecting, by employing the processor and the memory, an optimized m/z tolerance value and an optimized Rt tolerance value by repeating the step of selecting the m/z tolerance parameter and Rt tolerance parameter and the step of determining the true matching rate; and generating, by employing the processor and the memory, an optimal list of matches among peaks across the aligned query list and the target peak list employing the optimized m/z tolerance value and the optimized Rt tolerance value as matching parameters.

According to yet another aspect of the present invention, a machine-readable data storage device embodying a program of machine-executable instructions to match peaks in liquid chromatography-mass spectroscopy (LC-MS) datasets from multiple runs is provided. The program includes the method that the system is configured to perform as described above.

DETAILED DESCRIPTION

Figure 1:
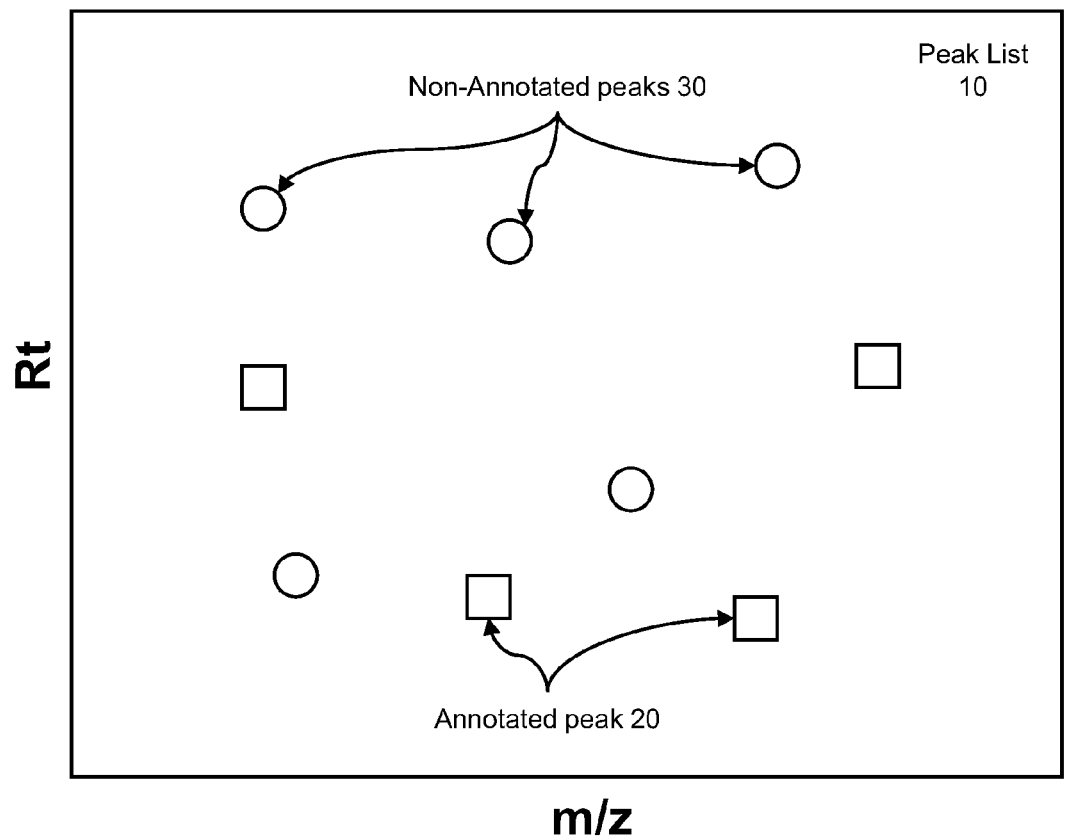
FIG. 1 is a schematic representation of a peak list or a feature list in two dimensions containing annotated and non-annotated features.

As stated above, the present invention relates to methods of matching peaks in datasets from a plurality of liquid chromatography-mass spectroscopy and apparatuses for the same, which are now described in detail with accompanying figures. Throughout the drawings, the same reference numerals or letters are used to designate like or equivalent elements. The drawings are not necessarily drawn to scale.

As used herein, "liquid chromatography-mass spectroscopy" (LC-MS) is any technique that employs liquid chromatography and any type of mass spectroscopy.

As used herein, a "liquid chromatography-mass spectroscopy apparatus," or an "LC-MS apparatus" is any apparatus that generates data on LC-MS of a sample.

As used herein, an "LC-MS run" is an experiment on an LC-MS apparatus that generates an "LC-MS dataset," i.e., a dataset representing the LC-MS data from the experiment.

As used herein, a "liquid chromatography-mass spectroscopy database," or an "LC-MS database" is any database that stores at least one dataset from any LC-MS runs.

As used herein, a "mass-to-charge ratio," or an "m/z" is the ratio of a mass to a charge of an ionized molecule or an ion as detected by a mass spectrometer in an LC-MS apparatus.

As used herein, a "retention time" is the time that a capillary column retains a particular compound that is detected as a peak in an LC-MS run. The retention time is the time between the starting time at which diffusion of a sample along a capillary column and the time at which an ionized molecule or an ion is detected by a mass spectrometer in an LC-MS apparatus.

As used herein, a "peak" is a data point from an LC-MS run and represents presence of at least one compound in the material of the sample of the LC-MS run at a mass-to-charge ratio and at a retention time. Each peak in an LC-MS dataset has a unique combination of values for its mass-to-charge ratio and its retention time.

As used herein, a "peak list" or a "feature list" is a list of peaks from at least one LC-MS run.

As used herein, an "annotated peak" is a peak for which the identity of the material represented by the peak is known.

As used herein, an "annotated peak list" is a list of annotated peaks.

As used herein, a "non-annotated peak" is a peak for which the identity of the material represented by the peak is unknown.

As used herein, a "non-annotated peak list" is a list of non-annotated peaks.

As used herein, a "mass shift" refers to shifting of every mass in the data from one LC-MS run by a number having a unit of Da. The number can be an integer.

As used herein, a "course grain search" refers to a search method in which a dataset is divided into large subsets. A course grain search on a dataset employs a fewer number of subsets than a fine grain search on the same dataset.

As used herein, a "fine grain search" refers to a search method in which a dataset is divided into small subsets. A fine grain search on a dataset employs a greater number of subsets than a course grain search on the same dataset.

As used herein, a "memory" refers to a device, an apparatus, or a manufactured physical structure that is configured to store information and allow retrieval of the information.

As used herein, a "processor device" refers to a device, an apparatus, or a manufactured physical structure that includes an electronic circuit for processing data.

Referring to FIG. 1, a schematic representation of a peak list 10, or a feature list, in two dimensions illustrates the data structure included in a peak list from an LC-MS run. One axis is a mass-to-charge ratio (m/z) axis. The other axis is a retention time (Rt) axis. Annotated peaks 20, i.e., annotated features, are shown as squares. The identity of the compound representing each annotated peak is known. Non-annotated peaks 30, i.e., non-annotated features, are shown in circles. The identity of the compound representing each non-annotated peak is unknown. Each peak can be represented as a two dimensional data point. Each peak can be represented a two-dimensional vector including two components, or can be represented by a point in a two-dimensional Cartesian coordinate.

In an embodiment of the present invention, a method that identifies common peaks among unidentified peaks in the datasets from different LC-MS or LC-MS/MS runs employs an algorithm, which is herein referred to as "Precision Peak Matching" or "PPM." The different runs can be from different laboratories, instruments, and biological samples that result in a significant variability in the data. PPM allows estimation and control of precision, defined as the fraction of truly identical peptide pairs among all pairs retrieved, in the matching process. PPM finds the maximal number of peptide pairs at a prescribed precision, thereby allowing quantitative control over the trade off between the number of true pairs missed, and false pairs found. PPM can find common peptides from a database of LC-MS runs of heterogeneous origins at a specified precision. PPM can fill a much-needed role in proteomics by extracting useful information from disparate LC-MS databases in a statistically rigorous and interpretable manner.

PPM can be employed to match any LC-MS data including data on peptides. PPM can extend the current peptide matching methods based on mass and retention time by estimating and controlling the mismatching rate, enabling it to compare not only similar LC-MS or LC-MS/MS runs, but also runs from different laboratories, instruments, and biological samples. PPM seeks the maximal number of matched peak pairs under a prescribed mismatching rate, and the estimation of this mismatching rate is essential to its strategy. PPM also estimates the precision of peak matching, defined as the fraction of matched peak pairs that are correct (i.e., identical), by matching two runs where the mass of one run is shifted.

PPM can find the maximal number of matched peaks between two runs at a prescribed precision. For each mass tolerance A and retention time tolerance B, PPM estimates the actual precision P by treating the number of matches with mass shift as false matches, denoted as M. Denote N as the number of matches without mass shift, then P=1−M/N. By searching over the parameter space of A and B, PPM maximizes N with the constraint that P is not below a prescribed precision.

PPM estimates the precision of peak matching, defined as the fraction of matched peak pairs that are correct (i.e., identical), by matching two runs where the mass of one run is shifted by a "mass shift" defined above. This approach is herein referred to as "mass shifting." For example, the mass of one LC-MS dataset can be shifted between 3 Da and 200 Da, although lesser and greater shifts can also be employed.

A formal description of PPM is provided herein. Let P denote the precision of peptide matching between runs j and l, each with nj and nl peaks, respectively, at mass tolerance A and retention time tolerance B. Let N denote the total number of matched peak pairs between j and l, M the total number of mismatches between them with a mass shift of dm, and $m_{ij}$ and $t_{ij}$ as the mass and retention time of the ith peak in run j, respectively. Then, $$N = \sum_{i=1}^{nj} \sum_{l=1}^{nl} f(m_{ij}, t_{ij}, m_{kl}, t_{kl}, A, B),$$

$$M = \sum_{i=1}^{nj} \sum_{l=1}^{nl} f(m_{ij} + dm, t_{ij}, m_{kl}, t_{kl}, A, B),$$

wherein the matching function $f(\ )$ is defined as:

$$f(m_{ij}, t_{ij}, m_{kl}, t_{kl}, A, B) = 1, \quad \text{Equation (1)}$$

$$\text{if } \left(\frac{m_{ij} - m_{kl}}{A}\right)^2 + \left(\frac{t_{ij} - t_{kl}}{B}\right)^2 \leq 1,$$

and $f(\ )=0$ otherwise.

Then the precision P is defined as:

$$P(j, l, A, B) = 1 - \frac{M}{N}, \quad \text{Equation (2)}$$

with its floor set at 0 and ceiling set at 1. Given a prescribed precision level $P_0$, PPM becomes the following optimization problem of maximizing N with variable A, B:

$$\text{Argmax}_{A\in(0,\infty), B\in(0,\infty)} \sum_{i=1}^{nj} \sum_{l=1}^{nl} f(m_{ij}, t_{ij}, m_{kl}, t_{kl}, A, B), \quad \text{Equation (3)}$$

subject to the constraint that $P(j,l,A,B) \geq P_0$. "Arg max" stands for "argument of the maximum," that is to say, the set of points of the given argument for which the value of the given expression attains its maximum value. Thus, the arg max function generates the maximum possible value under the conditions allowed to the arguments.

PPM is implemented by a systematic search strategy to find the optimal mass and retention time tolerance, which uses coarse grain search first followed by fine grain search. The input for PPM is two aligned peak lists from two LC-MS or LC-MS/MS runs, where each peak has a mass, retention time and intensity value. To correct for retention time drift between runs, the peak lists are assumed to be already aligned against each other. The output from PPM is a list of peak pairs where each pair of peaks are from two runs and are of the same chemical species, at a prescribed precision level. The number of such peak pairs is maximized by PPM under the constraint of the prescribed precision level.

Figure 2:
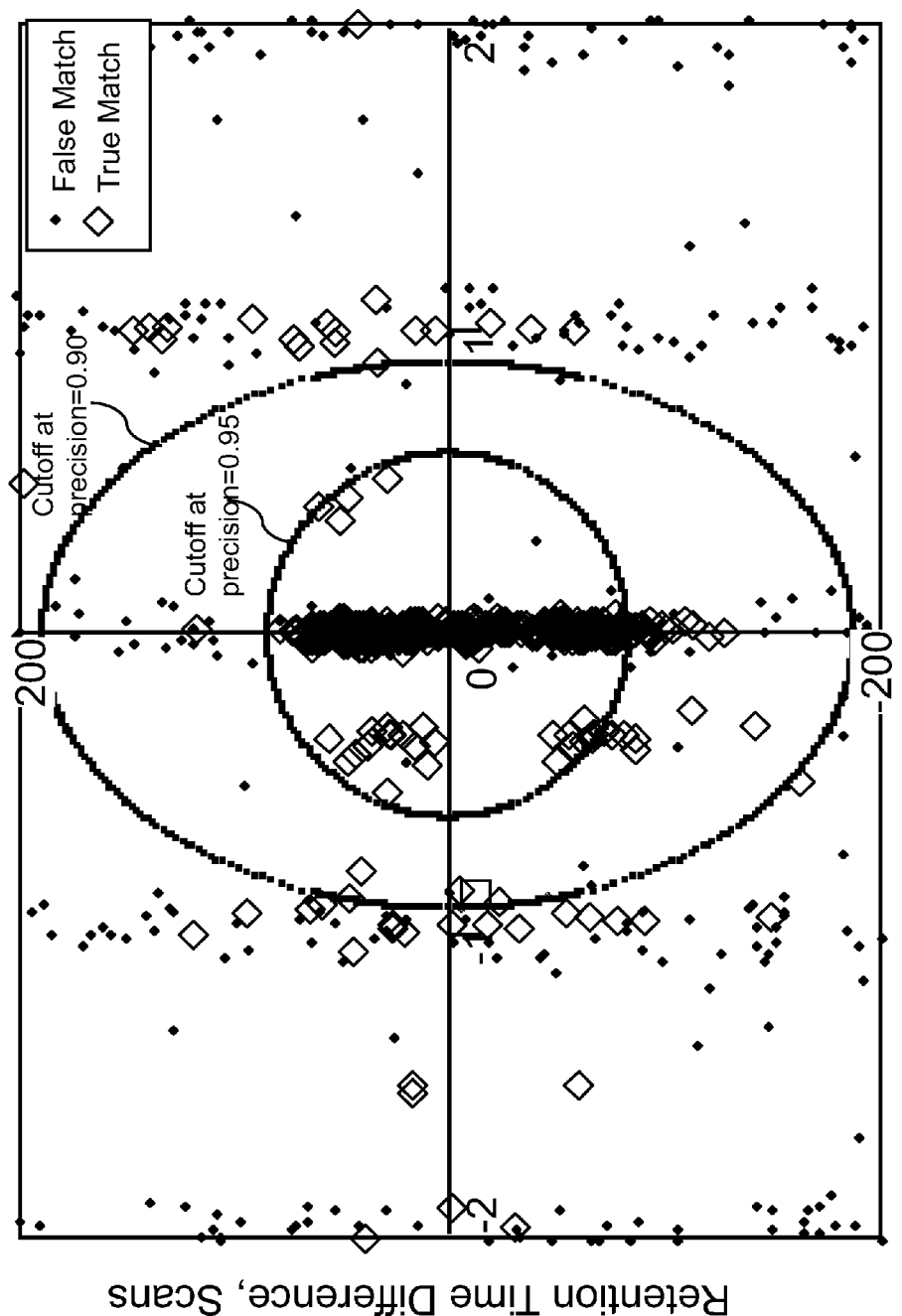
FIG. 2 is a schematic representation of peaks with true match and peaks with false match in the two-dimensional space in which the x-axis is a pairwise mass difference and the y-axis is a pairwise retention time difference.

Referring to FIG. 2, peaks with true match and peaks with false match from two LC-MS runs are schematically illustrated in the two-dimensional space in which the x-axis is the pairwise mass difference and the y-axis is the pairwise retention time difference. True matches do not require a mass shift to produce a match. False matches require a mass shift to produce a match. True matches are shown in large open diamond symbols and false matches are shown as small filled diamond symbols, respectively. PPM works by finding the optimal boundary of similarity cutoffs in mass and retention time.

The boundary is a closed line in the two-dimensional space. PPM can employ an ellipse decision boundary found by PPM. In this case, PPM uses an ellipse boundary around the origin. Peak pairs within the boundary are considered to be the same chemical species. PPM can adjust the long and short semiaxes of the ellipse during optimization. To achieve the prescribed precision, PPM estimates the precision for any ellipse boundary using mass shift. An exemplary ellipse decision boundary that provides a precision P of 0.95 and another exemplary ellipse boundary that provides a precision P of 0.90 are shown. PPM can also employ any other type of shapes for the boundary, including a rectangle in the two-dimensional space in which the x-axis is a pairwise mass difference and the y-axis is a pairwise retention time difference.

Figure 3:
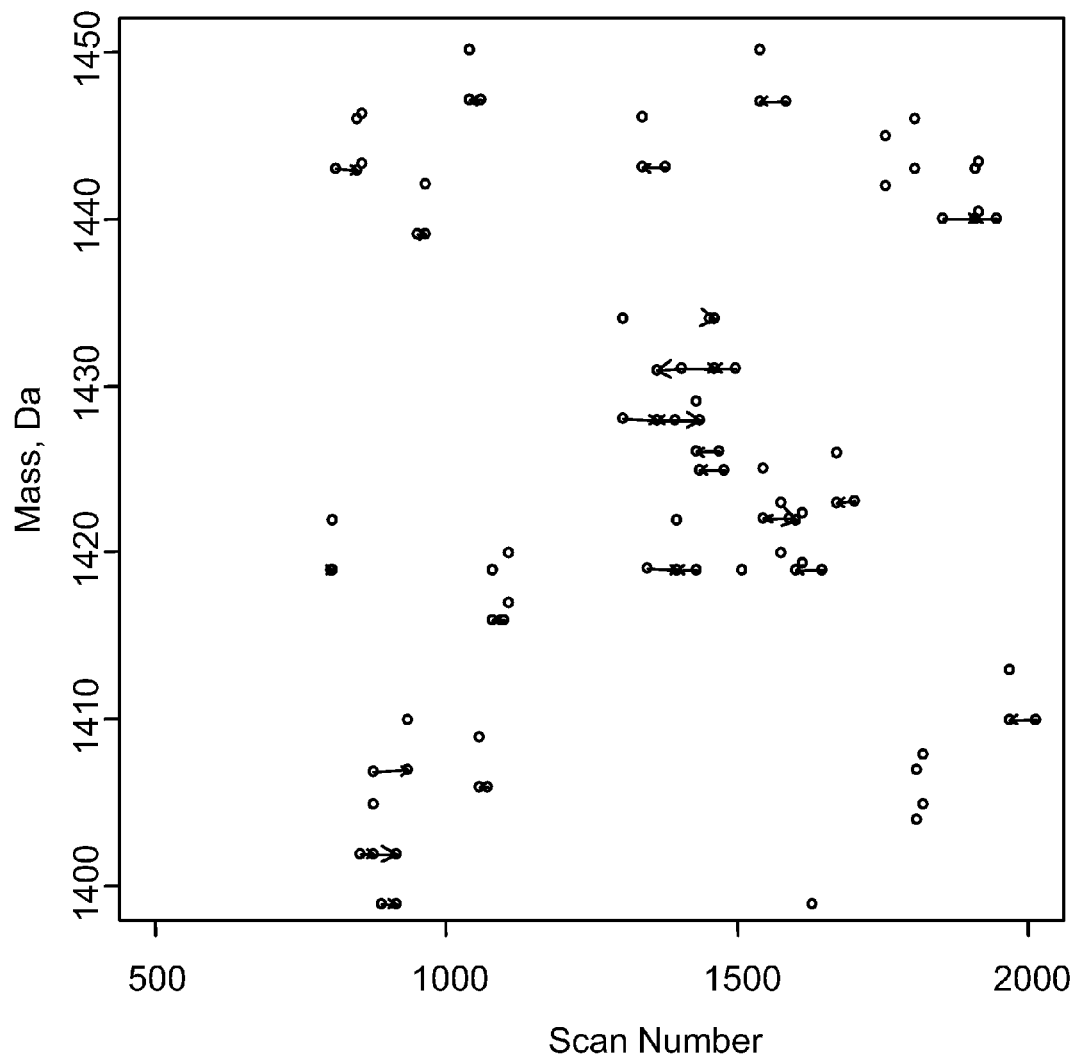
FIG. 3 is a graph schematically illustrating mass shifting employed to effect a false match.

Referring to FIG. 3, a graph schematically illustrates mass shifting. In an exemplary peak matching employing the method of an embodiment of the present invention, peptide matching based on similarity in mass and retention time for two LC-MS runs was performed. In this exemplary peak matching, two peptides from two runs are considered a match if their masses are within 0.2 Da of each other's mass and a retention time difference is within 60 scans. The peaks from the two runs are plotted together. The arrows (total 24) connect matched peptides. The mass of some of the peptides in the second run with each mass was incremented by 3 Da to effect the match.

The precision within an ellipse boundary can be estimated by shifting every mass of one run by a small integer amount. Within the boundary, if the total number of matches is defined as T, and the number of false matches is defined as NF, then the precision of match can be estimated as 1−(NF/T). In FIG. 3, the precision is 1−(5/24)=79%. Furthermore, the error bars of the precision can be estimated by using multiple mass shifts.

Because PPM can estimate the precision for every ellipse boundary, it can then adjust the long and short semiaxes of the ellipse to maximize the total number of matches. The total number of matches can be represented, for example, by the total number of points within a boundary ellipse as illustrated in FIG. 2, subject to the constraint that the estimated precision is not less than the prescribed precision level. The constrained optimization problem can be solved by using coarse grain search first, followed by a fine grain search around the previously found minima. Depending on the data, there is no guarantee that the desired boundary exist. Error bars of the precision can be useful guides, especially when the peaks are sparse.

Figure 4:
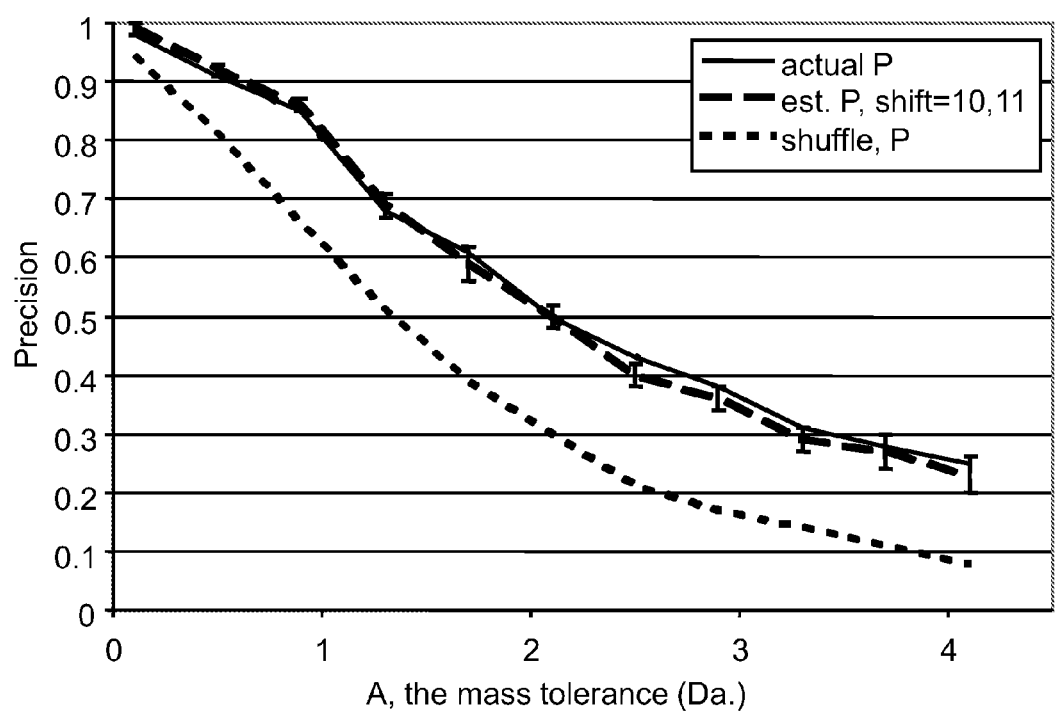
FIG. 4 is a graph illustrating that estimated precision according to the present invention matches true precision more closely than estimated precision provided by shuffle methods.

FIG. 4 is a graph illustrating that estimated precision according to an embodiment of the present invention matches true precision more closely than estimated precision provided by shuffle methods. Precision estimated by mass shifting is consistent with actual precision. FIG. 4 is a graph of Precision vs. A, in which A is the mass tolerance for the first two runs of an 18-mix sample, i.e., a sample having 18 compounds. B is the retention time tolerance, and is set to be proportional to A at a ratio of 300 scans/Da. The curve labeled "est P" represents precision P as defined above, and is calculated by using mass shifts of 10, −10, 11, and −11 Da. Error bars represent one standard deviation (SD). The curve labeled "shuffle P" is a curve that is calculated by randomly shuffling the retention times of one run with masses fixed, and counting the number of matches as mismatches in the manner known in the art. Methods of an embodiment of the present invention can improve estimation of precision of matches more accurately than prior art methods.

Because PPM can compare two LC-MS runs by adjusting the mass and retention time tolerance to fit prescribed precision, it can be a search tool to compare a query run against a database of runs, which can be similar runs in the same experiment, historical runs from the same or different laboratories. In the course of the research leading to the present invention, it has been demonstrated that PPM can work with heterogeneous runs from different labs.

Thus, mass shifting with appropriate shift amount can help estimate precision in peak matching. PPM maximizes the number of matches at a prescribed precision by adjusting the values of mass and retention time tolerance on the fly. PPM can serve as a search tool to compare a query run against a database of runs for finding common peptides or similar runs, including runs of heterogeneous origin. Methods of employing PPM to find matching peaks from two different LC-MS runs are described employing various flow charts.

Figure 5:
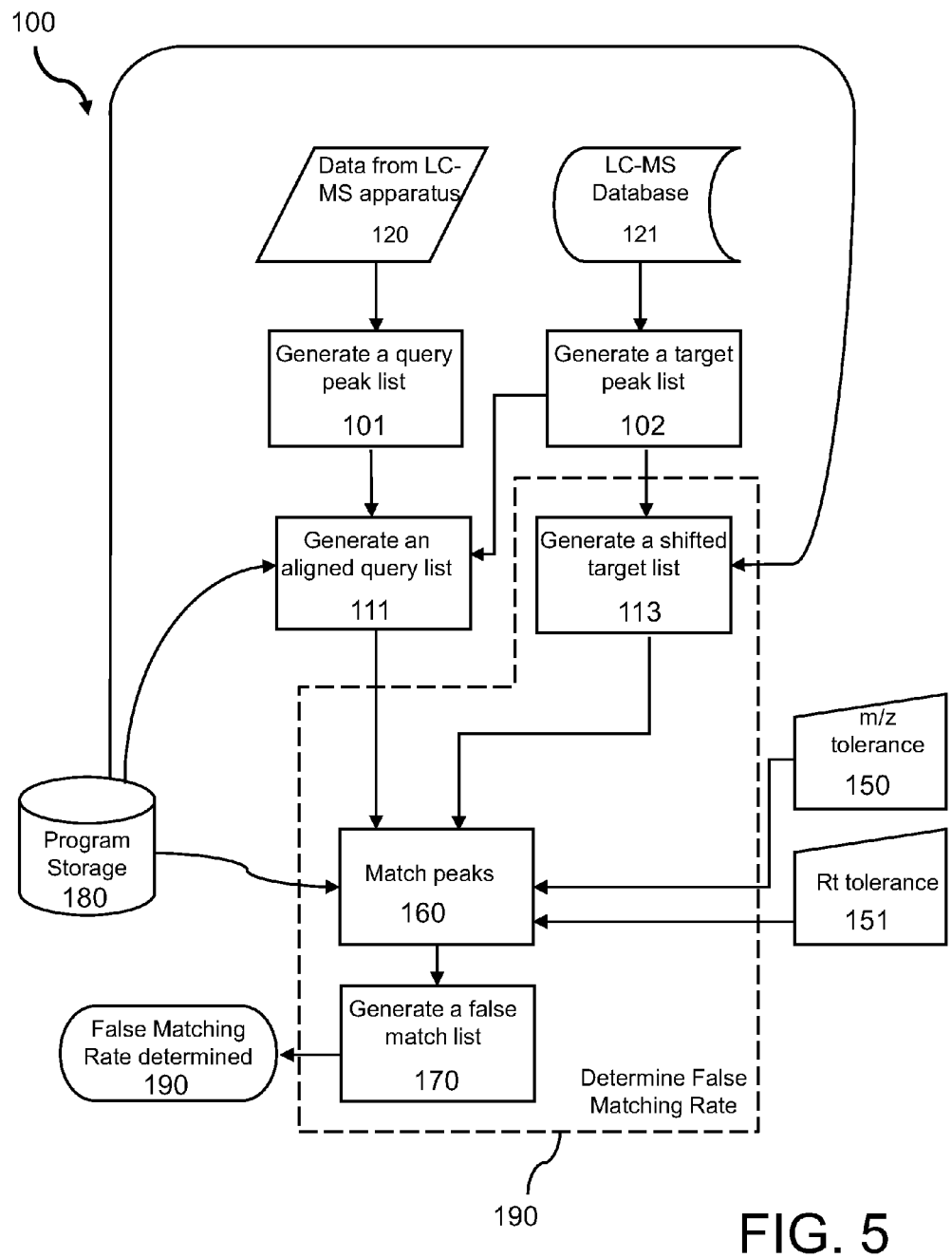
FIG. 5 is a first flow chart illustrating a method for determining a false matching rate once an m/z matching tolerance and an Rt matching tolerance are set.

Referring to FIG. 5, a first flow chart 100 illustrates a method for determining a false matching rate once an m/z matching tolerance and an Rt matching tolerance are set. Referring to step 120, a first dataset is provided, for example, from an LC-MS apparatus. The first dataset can be fetched from the LC-MS apparatus to a computing device such as a computer, for example, by electronic transmission or via a data storage medium such as a flash drive, a CD ROM, or a DVD ROM. The computing device can include a memory and a processor device in communication with the memory. Alternately, the first dataset can be fetched from an LC-MS database. Referring to step 121, a second dataset is provided, for example, from an LC-MS database. The second dataset can be fetched from the LC-MS database to the computing device via electronic transmission employing any transmission protocols, e.g., over the internet. The LC-MS database from which the second dataset is fetched can be the LC-MS database from which the first dataset is fetched, or can be a different LC-MS database. Alternately, the second dataset can be fetched from an LC-MS apparatus. The first and second datasets are fetched from the same LC-MS apparatus or different LC-MS apparatuses.

Referring to step 101, a query peak list is generated from the first dataset. The query peak list includes only the peaks for which the matching peaks are to be subsequently searched within the second dataset. The query list can include all of the peaks in the first dataset, or can include a subset of the first dataset that is less than the first dataset. The query list may be a subset of the original peaks based on intensity, m/z or Rt.

Referring to step 102, a target peak list is generated from the second dataset. The target peak list is a list of peaked to be queried for in the second dataset. There can be a one-to-one correspondence between all of the peaks in the target peak list and all of the peaks in the query peak list generated at step 101.

Referring to step 111, an aligned query list is generated from the query peak list. The query peak list is aligned to correct for retention time drift between LC-MS runs. The alignment process can provide a linear compensation for retention time to the peaks in the query peak list within a range of retention time as provided in the first dataset. A program storage device 180 can provide program instructions and/or a parameter set for effecting the generation of the aligned query list. In one embodiment, the target peak list generated at step 102 can provide data to be used as an alignment parameter.

Referring to step 113, a shifted target list is generated by performing at least one mass shift to the target peak list. The program storage device 180 can provide program instructions and/or a parameter set for effecting the generation of the shifted target list. The shifted target list can include peaks that are mass-shifted, i.e., peaks on which a mass shift is performed. In one embodiment of the present invention, all charges can be assumed to be a unit charge in the mass-to-charge ratio data. The mass shift can be performed for mass-to-charge ratio if the mass cannot be separated from the charge. The amount(s) of mass shift can be predetermined, or can be determined based on the nature of the first dataset and the second dataset. The amount of mass shift can be, for example, from 3 Da to 200 Da, although lesser and greater mass shifts are also contemplated herein. Integer mass shifts may be preferable since peptide features tend to be spaced at intervals of approximately 1 Da.

The peaks in the shifted target list can be mass-shifted by the same mass-differential or by the same mass-to-charge differential between each pair of an original peak and a shifted peak. In this case, the amount of mass shift is recorded and the shifted target list can include a two-dimensional vector for each shifted peak, in which the two-dimensional vector includes a shifted mass-to-charge ratio component and a retention time component.

The shifted target list can have multiple mass-shifted from each original peak such that each mass-shifted peak from the same original peak is shifted by different mass-to-charge differentials or by different mass differentials between each pair of the original peak and one of the shifted peaks. The shifted target list can include a three-dimensional vector for each shifted peak, in which the three-dimensional vector includes a shifted mass-to-charge ratio component, a retention time component, and a third component representing the amount of mass shift or the amount of mass-to-charge shift.

Referring to step 160, peaks are matched between the aligned query list and the shifter target list. The "Precision Pair Matching" (PPM) method described above is employed to perform peak matching between the aligned query list generated at step 111 and the shifted target list generated at step 113. The program storage device 180 can provide program instructions and/or a parameter set for effecting PPM. In one embodiment, the program storage device can provide a value for a mass-to-charge ratio (m/z) tolerance parameter and a value for a retention time (Rt) tolerance parameter. Alternately, the PPM parameters, i.e., a value for the m/z parameter and a value for Rt parameter, can be provided externally. For example, step 150 and step 151 can be employed to manually input a value for the m/z tolerance parameter and a value for the Rt tolerance parameter, respectively.

Referring to step 170, a false match list is generated based on the matching of peaks between the aligned query list and the shifter target list. The algorithm of PPM as described above determines false matches, i.e., matches that require a mass shift. The algorithm generates a false match list, i.e., a list of false matches as illustrated above by an example in FIG. 2. Step 113, step 160, and step 170 are collectively referred to as step 190, in which the false matching rate is determined based on the aligned query list from step 111 and the target peak list from step 102.

Referring to step 190, the false match rate is calculated based on the false match list from step 170. The false matching rate is determined under the condition of the given value of the m/z parameter and the given value for the Rt parameter, which are provided either by the program storage device 180 or by step 150 and 160. As discussed above, the false matching rate is a ratio of a total number of matches that requires a mass shift to achieve a match to a total number of matches in peaks. The false matching rate provided as an output of the first flow chart 100.

Figure 6:
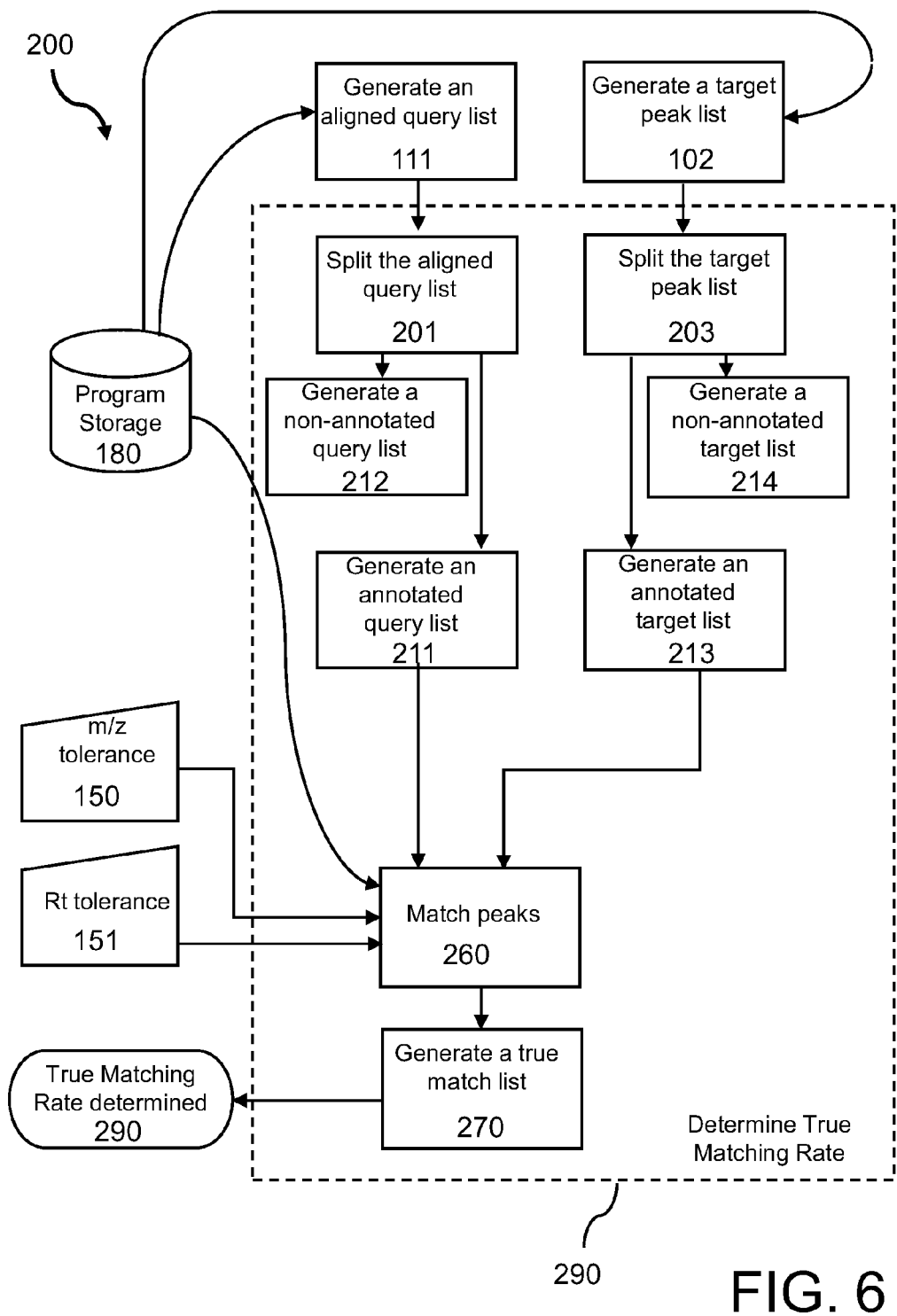
FIG. 6 is a second flow chart illustrating a method for determining a true matching rate when an m/z matching tolerance and an Rt matching tolerance are provided.

Referring to FIG. 6, a second flow chart 200 illustrates a method for determining a true matching rate when an m/z matching tolerance and an Rt matching tolerance. The second flow chart 200 can employ step 111 for generating an aligned query list, step 102 for generating a target peak list, step 150 for providing a manual input for the m/z tolerance parameter, step 151 for providing a manual input for the Rt tolerance parameter, and the program storage device 180 that are described above.

Referring to step 201, the aligned query list from step 111 is split into an annotated query list and a non-annotated query list. The non-annotated query list is generated, and can be stored, at step 212. The annotated query list is generated at step 211, and is forwarded to step 260.

Referring to step 203, the target peak list from step 102 is split into an annotated target list and a non-annotated target list. The non-annotated target list is generated, and can be stored, at step 214. The annotated query list is generated at step 213, and is forwarded to step 260.

Referring to step 260, peaks are matched between the annotated query list and the annotated target list employing the method of PPM as described above. The peaks are matched only for true matches, i.e., for matches that do not require any mass shift. False matches, i.e., matches that require a mass shift, are discarded at this step.

Referring to step 270, a true match list is generated based on the matching of peaks between the annotated query list and the annotated target list.

Referring to step 280, the true matching rate is determined from the true match list. The true matching rate is a ratio of a total number of matches that does not require a mass shift to achieve a match to a total number of matches in peaks.

Figure 7:
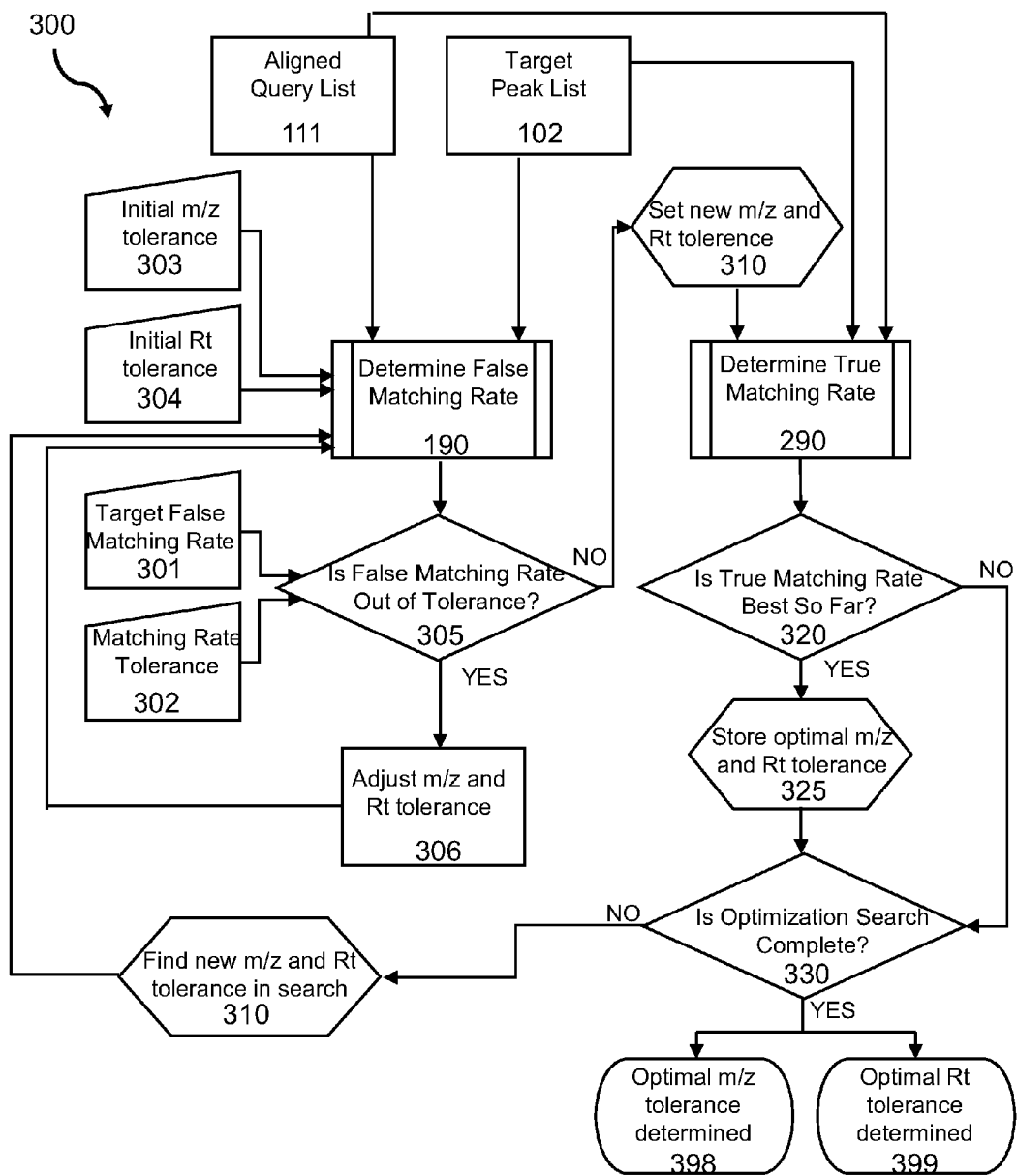
FIG. 7 is a third flow chart illustrating a method for determining an m/z matching tolerance and an Rt matching tolerance at a specified target false matching rate and a specified false matching rate tolerance.

Referring to FIG. 7, a third flow chart 300 illustrates a method for determining an m/z matching tolerance and an Rt matching tolerance at a specified target false matching rate and a specified false matching rate tolerance. The method of the third flow chart 300 employs methods described in the first and second flow charts (100, 200) as described above. A program storage device (not shown) can perform the same functions as the program storage device 180 in FIGS. 5 and 6, and can provide additional program instructions to other steps as needed.

Referring to steps 111 and 102, an aligned query list and an aligned target list are generated as described in the first flow chart 100.

Referring to steps 190, 303, 304, 305, 306, 301, 302, and 310 collectively, a mass-to-charge ratio (m/z) tolerance parameter and a retention time (Rt) tolerance parameter that satisfy a specification input criterion for a false matching rate between the aligned query list and the target peak list. The generation of the m/z tolerance parameter and the Rt tolerance parameter that satisfy the specification input criterion can be generated by a single pass through steps 190 and 305, respectively, or can be generated by multiple passes through an iterative process.

Specifically, the generation of the m/z tolerance parameter and the Rt tolerance parameter can be effected as follows. Referring to step 190, a false matching rate is determined by matching the aligned query list and the target peak list as described in the first flow chart 190. As a parameter for calculation of the false matching rate, an initial mass-to-charge ratio (m/z) tolerance is provided as an initial value for a mass-to-charge ratio tolerance parameter at step 303, and an initial retention time (Rt) tolerance is provided as an initial value for a retention time tolerance parameter at step 304.

Referring to step 305, the false matching rate that is calculated at step 190 is compared with the specification input criterion for the false matching rate. The specification input criterion for the false matching rate can be provided by a manual input step 301 for providing a target false matching rate TFMR as an input and another manual input step 302 for providing a false matching rate tolerance FMRT. In this case, the specification range for the false matching rate is between TFMR−FMTR and TFMR+FMTR. The specification range for the false matching rate is bound by 0 and 1. A specification range for the false matching rate can be from 0.01 to 0.2, and typically from 0.03 to 0.1, although lesser and greater values for the specification range can be employed. The specification input criterion can be provided as a single range for acceptable values for the false matching rate, or can be a plurality of specification input criteria for the value of the false matching rate. At this point, an initial false matching rate between the aligned query list and the target peak list is determined at step 305 employing the initial m/z tolerance parameter and the initial Rt tolerance parameter.

At step 305, the algorithm of the third flow chart 300 causes determination of whether the initial false matching rate satisfies the specification input criterion.

Referring to step 306, if the initial false matching rate does not satisfy the specification input criterion, the initial m/z tolerance parameter and the initial Rt tolerance parameter are adjusted to generate a revised m/z tolerance parameter and a revised Rt tolerance parameter, respectively. The revised m/z tolerance parameter is a newly assigned value for the m/z tolerance parameter, and the revised Rt tolerance parameter is a newly assigned value for the Rt tolerance parameter. A systematic method for determining the values for the revised m/z tolerance parameter and the revised Rt tolerance parameter can be provided by program instructions from a program storage device (not shown). Any method for determining the values for the revised m/z tolerance parameter and the revised Rt tolerance parameter can be employed, including, for example, comparison of the specification input criterion for the false matching rate and the value of the initial false matching rate.

The process flow then proceeds to step 190. The algorithm of step 190 performs a calculation to determine a revised false matching rate between the aligned query list and the target peak list employing the revised m/z tolerance parameter and the revised Rt tolerance parameter. The same algorithm is employed as at the first pass through step 190 with different values for the m/z tolerance parameter and the Rt tolerance parameter.

The steps 190, 305, and 306 are repeated until a revised false matching rate, which is calculated at each additional pass through step 190, satisfies the specification input criterion for the false matching rate. The revised m/z tolerance parameter and the revised Rt tolerance parameter are cumulatively adjusted revised at each pass through step 306. A revised false matching rate is determined employing a most recent revised m/z tolerance parameter and a most recent revised Rt tolerance parameter at each pass through step 190. The step of adjusting the revised m/z tolerance parameter and the revised Rt tolerance parameter, i.e., step 306, and the step of determining the a revised false matching rate, i.e., step 190, are repeated iteratively until the revised false matching rate satisfies the specification input criterion as determined at step 305.

If the false matching rate, whether it is an initial false matching rate or a revised false matching rate, satisfies the specification input criterion at step 305, the process flow proceeds to step 310. At step 310, the most recent value of the m/z tolerance parameter and the most recent value of the Rt tolerance parameter are set as a new m/z tolerance parameter and a new Rt tolerance parameter, respectively. The m/z tolerance parameter and the new Rt tolerance parameter are initial values for an m/z tolerance parameter and an Rt tolerance parameter to be employed at step 290.

Referring to step 290, a true matching rate between the aligned query list and the target peak list is determined employing the m/z tolerance parameter and the Rt tolerance parameter, of which the values are set at step 290. Steps 111 and 102 provide the aligned query list and the target peak list to step 290. The step 290 performs the same operation as in the second flow chart 200. A value for the true matching rate is calculated at step 290 as described above.

Referring to step 320, the value for the true matching rate from step 290 is compared with a stored value for the true matching rate from a previously determination of the true matching rate. If the value for the true matching rate is greater than or equal to the stored value, the process flow proceeds to step 325. At step 325, the stored value for the true matching rate is updated with the value for the true matching rate as provided at step 290 in the most recent calculation, i.e., with the current value for the true matching rate at step 320. At the same time, a value for the m/z tolerance parameter is stored as a "stored m/z tolerance parameter," and a value for the Rt tolerance parameter is stored as a "stored Rt tolerance parameter."

To insure that the value for the true matching rate at the first pass through step 320 is stored as the stored value for the true matching rate at step 325, the initial value for the true matching rate can be set to 0 for the purpose of comparison at step 320. Alternately, a counter for tracking the number of passes through step 320 can be employed to trigger storage of the value for the true pass rate at step 325 if the pass count is 1, i.e., for the first pass through step 320.

If the value for the true matching rate is lesser than the stored value for the true matching rate, which can be 0 for the first pass through step 320 or a value stored at a previous pass through step 325, the process flow proceeds to step 330. In this case, the stored value for the true matching rate is not updated with the value. Correspondingly, the stored m/z tolerance parameter is not updated and the stored Rt tolerance parameter is not updated. If the most recent value for the true matching rate is less than the stored value for the true matching rate, the most recent values for the m/z tolerance parameter and the Rt tolerance parameter are "inferior" to the stored values for the m/z tolerance parameter and the Rt tolerance parameter, i.e., the stored m/z tolerance parameter and the stored Rt tolerance parameter. In this case, the stored results from one of the previous passes through step 320 provide a higher value for the true matching rate, i.e., provides a "superior" matching of peaks. Thus, the stored m/z tolerance parameter and the stored Rt tolerance parameter are preserved without a change.

Referring to step 330, the algorithm of an embodiment of the present invention determines whether an optimization search is complete. The step 330 can be performed immediately after step 320 if the stored m/z tolerance parameter and the stored Rt tolerance parameter are not updated, or can be performed after step 325 if the stored m/z tolerance parameter and the stored Rt tolerance parameter are updated. The determination on whether the optimization search is complete can be based on a predefined criterion including at least one of a number of iterations at the step of comparing the value with the stored value, a history of the stored value for the true matching rate, a history of the stored m/z tolerance parameter, and a history of the stored Rt tolerance parameter.

If the optimization search is determined to be complete at step 330, the process flow proceeds to steps 398 and 399 in parallel. At step 398, an optimized m/z tolerance value is generated, which is the same as the current value for the stored m/z tolerance parameter. At step 399, an optimized Rt tolerance value is generated, which is the same as the current value for the stored Rt tolerance parameter.

If the optimization search is determined to be incomplete at step 330, the process flow proceeds to step 310. At step 310, another value is assigned for each of the m/z tolerance parameter and the Rt tolerance parameter. The newly assigned values for the m/z tolerance parameter and the Rt tolerance parameter can be generated by the program storage device (not shown) based on the stored values for the true matching rate, the m/z tolerance parameter stored at step 325, and/or the Rt tolerance parameter stored at step 325. Alternately or additionally, the newly assigned values for the m/z tolerance parameter and the Rt tolerance parameter can be provided as a manual input.

The process flow then proceeds to step 190 to determine a false matching rate employing the m/z tolerance parameter and the Rt tolerance parameter as provided at step 310. The process flow then proceeds to step 305 to determine whether the false matching rate as determined at step 190 in the most recent pass satisfies the specification input criterion.

Depending on the outcome at step 305, the process flow can proceed to step 310 or to step 306 at least once more. At step 306, at which the m/z tolerance parameter and the revised Rt tolerance parameter are adjusted until the false matching rate satisfies the specification input criterion. The step of determining the true matching rate between the aligned query list and the target peak list employing the m/z tolerance parameter as adjusted and the Rt tolerance parameter as adjusted, i.e., step 190, can also be repeated until the false matching rate satisfies the specification input criterion.

Referring to steps 320, 325, 330, 398, 399, 310, 190, 305, 306, 310, and 290 collectively, an optimized m/z tolerance value and an optimized Rt tolerance value are selected by repeating the step of selecting the m/z tolerance parameter and Rt tolerance parameter as performed at steps 190, 305, and 310, and the step of determining the true matching rate as performed at step 290. Further, the step of adjusting the revised m/z tolerance parameter and the revised Rt tolerance parameter, i.e., step 306, and the step of determining a revised false matching rate until the revised false matching rate satisfies the specification input criterion, i.e., steps 190 and 205 collectively, can be repeated to select the optimized m/z tolerance value and the optimized Rt tolerance value.

Figure 8:
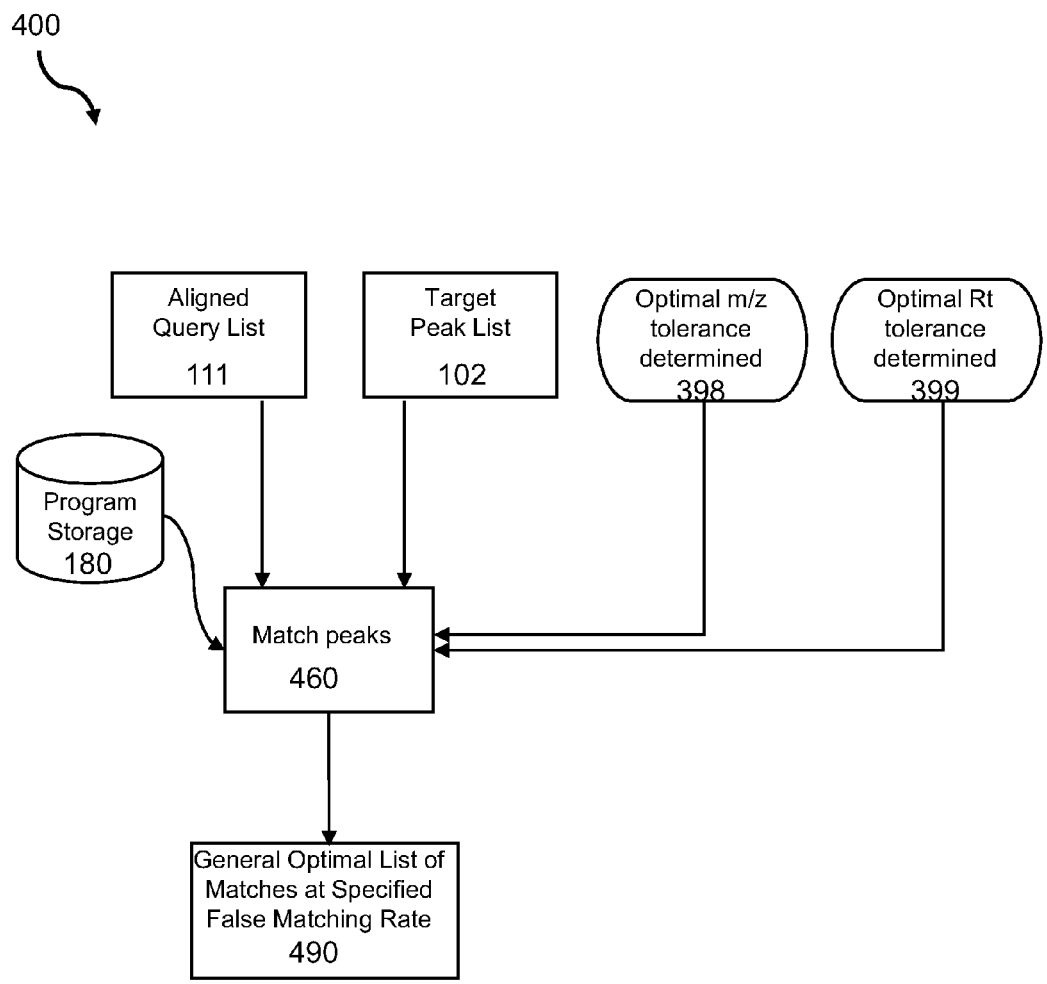
FIG. 8 is a fourth flow chart illustrating a method for generating an optimal list of matches once the optimal m/z tolerance value and the optimal Rt tolerance value are determined.

Referring to FIG. 8, a fourth flow chart 400 illustrates a method for generating an optimal list of matches once the optimal m/z tolerance value and the optimal Rt tolerance value are determined. Referring to step 460, peaks are matched between the aligned query list from step 111 and the target peak list from step 102 employing the method of PPM described above. The optimal m/z tolerance value from step 398 and the optimal Rt tolerance value from step 399 are employed as a matching parameter for PPM.

Referring to step 490, an optimal list of matches among peaks across the aligned query list and the target peak list is generated employing the optimized m/z tolerance value and the optimized Rt tolerance value as matching parameters. The optimal list of matches is the output of the algorithm according to an embodiment of the present invention. The optimal list of matches includes a dataset on peaks. The dataset on peaks includes at least a calculated m/z and Rt for each peak.

Figure 9:
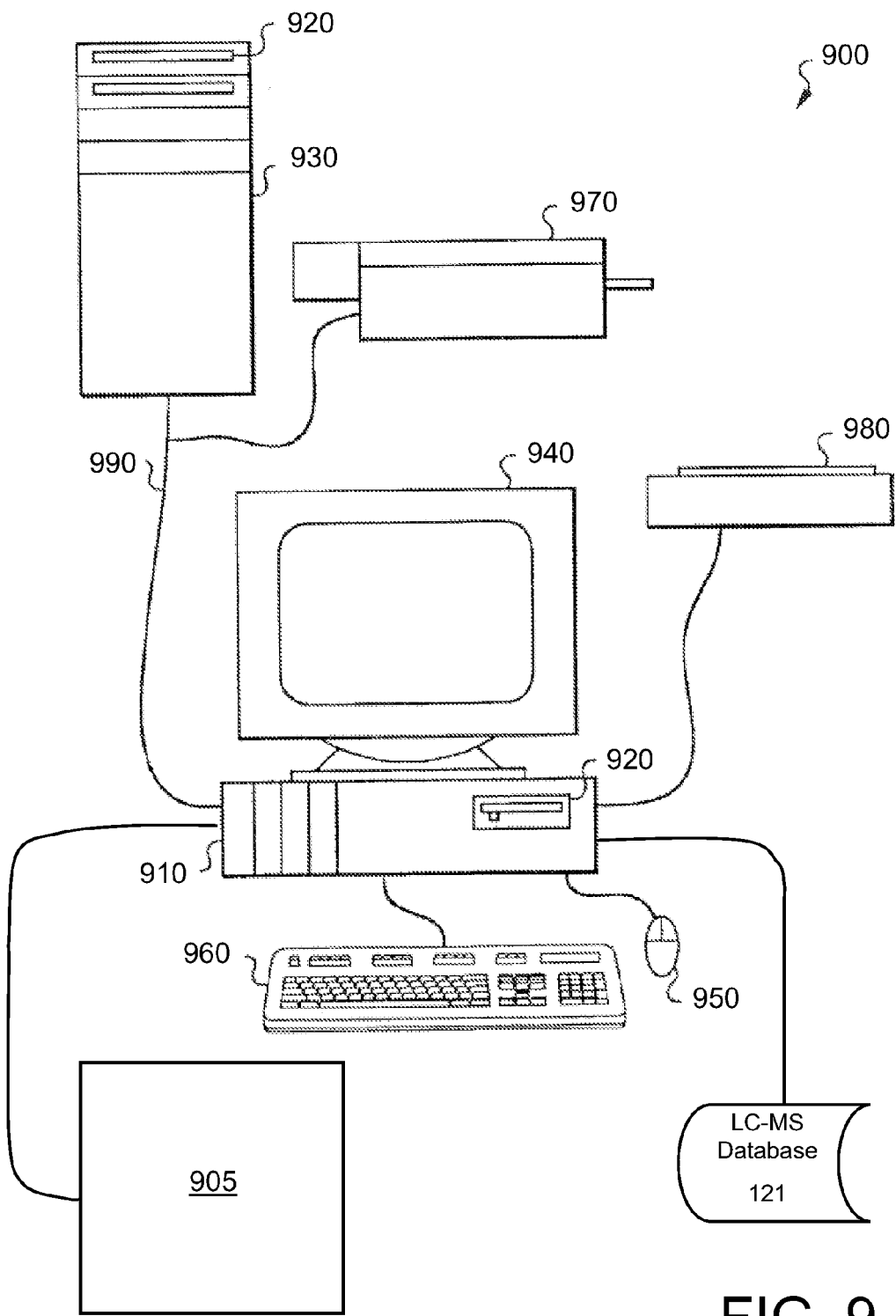
FIG. 9 illustrates an exemplary system according to an embodiment of the present invention.

Referring to FIG. 9, an exemplary system 900 according to the present invention is shown. The exemplary system 900 can be employed for matching peaks in liquid chromatography-mass spectroscopy (LC-MS) datasets from multiple runs. The exemplary system includes a computing device that is configured to perform program instructions. The computing device can include a memory and a processor device in communication with the memory. The program instructions can configure the computing device to perform the steps of embodiments of the present invention described above. The exemplary system 900 can be a computer-based system in which the methods of the embodiments of the invention can be carried out by an automated program of machine-executable instructions to match peaks in liquid chromatography-mass spectroscopy (LC-MS) datasets from multiple runs.

A data storage device that is programmable and readable by a machine and tangibly embodying or storing a program of instructions that are executable by the machine to perform the methods described herein are also provided. For example, the automated program can be embodied, i.e., stored, in a machine-readable data storage devices such as a hard disk, a CD ROM, a DVD ROM, a portable storage device having an interface such as a USB interface, a magnetic disk, or any other storage medium suitable for storing digital data.

The computer-based system includes a processing unit 910, which is a computing device and houses a processor device, a memory and other systems components (not shown expressly in the drawing) that implement a general purpose or special purpose processing system, or computer that can execute a computer program product. The computer program product can comprise media, for example a compact storage medium such as a compact disc, which can be read by the processing unit 910 through a disc drive 920, or by any means known to the skilled artisan for providing the computer program product to the general purpose processing system for execution thereby. The exemplary system 900 can include an LC-MS apparatus 905 and/or an LC-MS database. Alternately, the LC-MS apparatus 905 and/or an LC-MS database 121 can be external to the exemplary system 900 and electronically connected through a wired network or a wireless network.

The computer program product can comprise all the respective features enabling the implementation of the inventive method described herein, and which is able to carry out the method when loaded in a computer system. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The computer program product can be stored on hard disk drives within the processing unit 910, as mentioned, or can be located on a remote system such as a server 930, coupled to the processing unit 910, via a network interface such as an Ethernet interface. A monitor 940, a mouse 950 and a keyboard 960 are coupled to the processing unit 910, to provide user interaction. A scanner 980 and a printer 970 can be provided for document input and output. The printer 970 is shown coupled to the processing unit 910 via a network connection, but can be coupled directly to the processing unit 910. The scanner 980 is shown coupled to the processing unit 910 directly, but it should be understood that peripherals might be network coupled, or direct coupled without affecting the ability of the processing unit 910 to perform the method of the invention.

While the present invention has been particularly shown and described with respect to preferred embodiments thereof, it will be understood by those skilled in the art that the foregoing and other changes in forms and details can be made without departing from the spirit and scope of the present invention. For example, variations that combine various steps of the first, second, and third exemplary programs in a single program can be employed. It is therefore intended that the present invention not be limited to the exact forms and details described and illustrated, but fall within the scope of the appended claims.

What is claimed is:

1. A method for matching peaks in liquid chromatography-mass spectroscopy (LC-MS) datasets from multiple runs, said method comprising steps of:
generating an aligned query list for peaks from a first dataset from a first LC-MS run;
generating a target peak list for peaks from a second dataset from a second LC-MS run;
generating a mass-to-charge ratio (m/z) tolerance parameter and a retention time (Rt) tolerance parameter that satisfy a specification input criterion for a false matching rate between said aligned query list and said target peak list;
determining a true matching rate between said aligned query list and said target peak list employing said m/z tolerance parameter and said Rt tolerance parameter;
determining an optimized m/z tolerance value and an optimized Rt tolerance value by repeating said step of generating said m/z tolerance parameter and Rt tolerance parameter and said step of determining said true matching rate; and
generating an optimal list of matches among peaks across said aligned query list and said target peak list employing said optimized m/z tolerance value and said optimized Rt tolerance value as matching parameters.

2. The method of claim 1, further comprising steps of:
fetching, by employing a processor and a memory in communication with said processor, said first dataset from an LC-MS apparatus or an LC-MS database; and
fetching, by employing said processor and said memory, said second dataset from said LC-MS apparatus, another LC-MS apparatus, said LC-MS database, or another LC-MS database.

3. The method of claim 1, wherein said step of generating said m/z tolerance parameter and said Rt tolerance parameter comprises steps of:
determining an initial false matching rate between said aligned query list and said target peak list employing an initial m/z tolerance parameter and an initial Rt tolerance parameter;
determining whether said initial false matching rate satisfies said specification input criterion; and
if said initial false matching rate does not satisfy said specification input criterion, adjusting said initial m/z tolerance parameter and said initial Rt tolerance parameter to generate a revised m/z tolerance parameter and a revised Rt tolerance parameter, respectively, and determining a revised false matching rate between said aligned query list and said target peak list employing said revised m/z tolerance parameter and said revised Rt tolerance parameter.

4. The method of claim 3, wherein said step of generating said m/z tolerance parameter and said Rt tolerance parameter comprises steps of:
adjusting said revised m/z tolerance parameter and said revised Rt tolerance parameter;
determining another revised false matching rate employing a most recent revised m/z tolerance parameter and a most recent revised Rt tolerance parameter; and
repeating said step of adjusting said revised m/z tolerance parameter and said revised Rt tolerance parameter and said step of determining said another revised false matching rate until said another revised false matching rate satisfies said specification input criterion.

5. The method of claim 1, further comprising a step of comparing a value for said true matching rate from said step of determining said true matching rate with a stored value for said true matching rate from a previously determination of said true matching rate, said stored value being stored in a data storage medium.

6. The method of claim 5, further comprising, if said value for said true matching rate is greater than said stored value, performing steps of:
updating said stored value with said value for said true matching rate;
storing in said data storage medium a value for said m/z tolerance parameter as a stored m/z tolerance parameter; and
storing in said data storage medium a value for said Rt tolerance parameter as a stored Rt tolerance parameter.

7. The method of claim 6, further comprising steps of:
determining whether an optimization search is complete after comparing said value with said stored value based on a predefined criterion comprising at least one of a number of iterations at said step of comparing said value with said stored value, a history of said stored value for said true matching rate, a history of said stored m/z tolerance parameter, and a history of said stored Rt tolerance parameter;
if said optimization search is complete, generating said optimized m/z tolerance value and said optimized Rt tolerance value, wherein said optimized m/z tolerance value is said stored m/z tolerance parameter and said optimized Rt tolerance value is said stored Rt tolerance parameter.

8. The method of claim 7, further comprising conditional steps of:
assigning another value for said m/z tolerance parameter and another value for said Rt tolerance parameter;
determining another false matching rate employing said m/z tolerance parameter and said Rt tolerance parameter; and
determining whether said another false matching rate satisfies said specification input criterion.

9. The method of claim 8, wherein said conditional steps further comprise:
adjusting said m/z tolerance parameter and said revised Rt tolerance parameter until said another false matching rate satisfies said specification input criterion; and
repeating said step of determining said true matching rate between said aligned query list and said target peak list employing said m/z tolerance parameter as adjusted and said Rt tolerance parameter as adjusted.

10. The method of claim 1, wherein said step of determining said true matching rate comprises a step of splitting said aligned query list into an annotated query list and a non-annotated query list.

11. The method of claim 10, wherein said step of determining said true matching rate further comprises a step of splitting said target peak list into an annotated target list and a non-annotated target list.

12. The method of claim 11, wherein said step of determining said true matching rate further comprises a step of matching peaks between said annotated query list and said annotated target list.

13. The method of claim 12, wherein said step of determining said true matching rate further comprises a step of generating a true match list based on said matching of peaks between said annotated query list and said annotated target list, wherein said true matching rate is determined from said true match list.

14. The method of claim 13, wherein said true matching rate is a ratio of a total number of matches that does not require a mass shift to achieve a match to a total number of matches in peaks.

15. The method of claim 1, wherein said step of generating said m/z tolerance parameter and said Rt) tolerance parameter comprises a step of generating a shifted target list by mass-shifting peaks in said target peak list.

16. The method of claim 15, wherein said step of generating said m/z tolerance parameter and said Rt) tolerance parameter further comprises a step of matching peaks between said aligned query list and said shifter target list.

17. The method of claim 16, wherein said step of generating said m/z tolerance parameter and said Rt) tolerance parameter further comprises a step of generating a false match list based on said matching of peaks between said aligned query list and said shifter target list, wherein said false match rate is calculated based on said false match list.

18. The method of claim 17, wherein said false matching rate is a ratio of a total number of matches that requires a mass shift to achieve a match to a total number of matches in peaks.

19. The method of claim 18, wherein said mass-shifting of said peaks in said target peak list shifts said peak by a mass between 3 Da and 200 Da.

20. The method of claim 1, wherein said optimal list of matches comprises data on peaks, said data on peaks comprising at least a calculated m/z and Rt for each peak.

* * * * *